(12) United States Patent
Apajalahti et al.

(10) Patent No.: US 7,014,863 B2
(45) Date of Patent: Mar. 21, 2006

(54) ADDITIVE FOR AN ANIMAL FEED

(75) Inventors: Juha Apajalahti, Helsinki (FI); Nina Rautonen, Espoo (FI); Michael Richard Bedford, Marlborough (GB)

(73) Assignee: Finfeeds International Limited, Marlborough ( * ) Notice: Subject to any disclaimer, the term of this patent is extended or adjusted under 35 U.S.C. 154(b) by 160 days.

(21) Appl. No.: 10/165,796

(22) Filed: Jun. 7, 2002

(65) Prior Publication Data

US 2003/0059498 A1    Mar. 27, 2003

Related U.S. Application Data

(63) Continuation of application No. PCT/EP00/12442, filed on Dec. 8, 2000.

(30) Foreign Application Priority Data

Dec. 9, 1999   (GB) .................................... 9929152

(51) Int. Cl.
    *A23K 1/17*     (2006.01)
(52) U.S. Cl. .................. 424/442; 424/94.1; 424/94.61; 424/94.63; 424/438; 426/2; 426/805; 426/807; 514/556
(58) Field of Classification Search ................ 424/405, 424/442, 438, 94.1, 94.63, 94.61; 426/2, 426/807, 805; 514/556
    See application file for complete search history.

(56) References Cited

U.S. PATENT DOCUMENTS 5,624,678 A * 4/1997 Bedford et al.

FOREIGN PATENT DOCUMENTS

| EP | 681787 | 11/1995 |
|---|---|---|
| JP | 01132533 | 5/1989 |
| JP | 01238538 | 9/1989 |
| JP | 08133911 | 5/1996 |
| WO | WO 94/24886 | 11/1994 |
| WO | WO 97/29645 | 8/1997 |
| WO | WO 98/24327 | 6/1998 |
| WO | WO 99/04784 | 2/1999 |

OTHER PUBLICATIONS

Merck Veterinary Manual pp 497-499 ,1967.*

* cited by examiner

*Primary Examiner*—Neil S. Levy
(74) *Attorney, Agent, or Firm*—Fitch, Even, Tabin & Flannery (57) ABSTRACT

The present invention relates to the use of a combination of a protease and an inner salt of a quaternary amine carboxylic acid for the preparation of an agent for the treatment and/or prophylaxis of coccidiosis and bacterial infections such as necrotic enterities in animals. Preferred embodiments of the invention comprise the inclusion of a xylanase and/or an α-amylase in the agent. A nutritional additive comprising a combination of an inner salt of a quaternary amine carboxylic acid protease and (optionally) a xylanase and an α-amylase is also disclosed. It can be used for improving the rate of weight gain of animals.

18 Claims, 3 Drawing Sheets

*Eimeria* challenge: bird weight at day 21

Detection of *C. perfringens* toxin gene in the ileum

| Lane: | 1 | 2 | 3 | 4 | 5 | 6 | 7 |
|---|---|---|---|---|---|---|---|
| | Calibration | No challenge | Eimeria challenge | *C. perfringens* challenge | Double challenge (Eimeria + *C. perfringens*) | Double challenge: feed incl. protease | Double challenge: feed incl. protease + betaine |

ADDITIVE FOR AN ANIMAL FEED

This is a continuation, of prior application number PCT/EP00/12442, filed Dec. 8, 2000, which is hereby incorporated herein by reference in its entirety.

This invention relates to an additive for an animal feed and particularly to such an additive which improves the rate of weight gain of an animal fed with a feed in which it is incorporated. It furthermore relates to such an additive which is useful for the treatment and/or prophylaxis of coccidiosis and/or a bacterial infection including those which can result in necrotic enteritis.

The farming of many different types of animals is important throughout the world for the production of food for human consumption. Whilst the animals are being reared, they can come into contact with a variety of infection-causing bacteria and parasites such as *Eimeria, Campylobacter, Clostridium, Salmonella, E. coli* and *Listeria*.

Coccidiosis is a common cause of disease in intensively-reared farm livestock, particularly in poultry. Coccidiosis is caused by a protozoa, a single-celled parasite, of the sub-phylum *Apicomplexa*. Many of the species that cause the disease in domestic animals belong to the genus *Eimeria*. The parasites multiply in the epithelium of the intestine. In chickens, seven species of *Eimeria* have been identified, five of which are considered to be pathogenic. These are *E. acervulina, E. maxima, E. necratrix, E. tenella* and *E. brunetti*.

Coccidia are ubiquitous organisms and are generally endemic wherever chickens are raised. Outbreaks of disease can vary from severe to very mild infections. Like many parasitic protozoa, the life cycle of *Eimeria* is relatively complex. Sexual and asexual multiplication occurs within the chickens' intestines. During this process of multiplication and development of the parasite, the host tissue is destroyed which leads to the various clinical manifestations observed in outbreaks of coccidiosis. The oocysts produced and excreted develop further outside the host where they may undergo further development and infect other chickens. Oocysts can in fact survive outside a host for a long period of time which enables them to infect other birds even after removal of the initially infected host. They may also be spread between flocks by other agents including people, pets, insects, rodents, dust and other birds.

Sporulated oocysts contain four sporocysts, each containing two sporozoites. These sporozoites are released by mechanical and enzymatical action in the digestive tract of the chicken. This enables them to invade the epithelial cells in the intestine or caeca depending on the *Eimera* species involved.

Although there are differences in pathogenicity between species and strains of *Eimeria,* the symptoms displayed by an infected animal may be one or more of the following: bloody droppings, high mortality, general lethargy, emaciation, a marked drop in feed consumption, diarrhoea and a drop in egg production. It has been estimated that coccidiosis is probably responsible for around 6–10% of unwanted mortality among poultry flocks. Additionally, sub-clinical disease increases feed conversion ratios (FCRs) and reduces performance. Accordingly, the economic consequences of this disease are considerable and most undesirable.

Various methods have been investigated to combat coccidiosis. Attempts have been made to control the disease through management strategies based on high standards of hygiene together with the use of chemical disinfectants in the environment of the poultry. However, even under scrupulously hygienic conditions, it has not been found possible to eradicate coccidiosis although such measures were found to lower the initial infection pressure in a poultry house. Both live and attenuated vaccines have been investigated as methods of control, but these are relatively expensive and tend to depress the growth rates of animals as a result of their action.

At present, coccidiosis in poultry is routinely controlled by the use of relatively costly preventative anticoccidial drug programmes. Such programmes attempt to restrict coccidial infections thus limiting the effects of sub-clinical outbreaks of disease. This is usually accomplished by the continuous inclusion of anticoccidial agents in the feed from early in the life of the flock until close to slaughter for broiler birds or by controlled withdrawal for layers. When first developed, such agents were used individually. This often resulted in strains of parasites developing drug-resistance. It is presently attempted to control coccidiosis by the continual introduction of new drugs or by the use of drug programmes involving rotational use of anticoccidial agents of different biochemical structures either during the grow-out period (shuttle programmes) or at frequent intervals (rotation programmes). In spite of the routine use of anticoccidial agents in poultry feeds, sub-clinical coccidiosis is still found on the majority of poultry farms.

Inner salts of quaternary amine carboxylic acids function as osmoprotectants. Such salts increase the osmotic strength of cells without adversely affecting enzyme activity, and they protect enzymes from ionic or temperature inactivation (Nash et al., Aust. *J. Plant Physiol.* 9:47–57 (1982); Yancey et al., *Science* 224:1064–1069 (1982); Rudolph et al., Archives *Biochem. Biophys.* 245:134–143 (1986); McCue & Hanson, *Trends in Biotechnology* 8:358–362 (1990); Papageorgiou et al., *Curr. Res. In Photosynthesis* 1:957–960 (1990)). While some organisms (and tissues) can accumulate inner salts such as betaine in high quantities under osmotic stress through osmotically induced synthesis, most animals lack this capability, and are dependent upon the intake of exogenous inner salts. For example, isolated salmon liver mitochondria, when exposed to osmotic stress, show increased betaine intake, but not synthesis (Bjorkoy, G., Synthesis and Accumulation of glycine betaine in Salmon (*Salmo salar*) and Mussels, MSc thesis, Norwegian College of Fisheries, University of Tromso, pp. 94).

The use of betaine for the treatment of coccidiosis is disclosed in U.S. Pat. No. 5,834,473. The combined use of betaine and a coccidiostat for the same purpose is taught by WO 94/24886. EP-A-0 681 787 suggests the use of enzymes such as a protease and/or a carbohydrase for the treatment and/or prevention of coccidiosis.

GB-A-2 327 345 teaches that bacterial infections in the ileum of livestock can be treated by incorporating enzymes in an animal feed which promote digestion of the feed. Such enzymes break down polysaccharides present in the cereal component of the feed into oligosaccharides which are used as a food source by host-beneficial microorganisms present in the gut. As a consequence of this proliferation, pathogenic bacteria cannot thrive due to the process of competitive exclusion. This strategy is generally more effective when the quality of food is low (Classen et al., *Proc. 2$^{nd}$ Eur. Symp. on Feed Enzymes,* 1995, 65; Pack and Bedford, *Poultry International,* 1998, 43).

JP-A-01 238538 and JP-A-01 132533 teach the combined use of betaine and various enzymes for improving the digestive function of animals. However, neither of these documents suggests to use such combinations for the treatment or prevention of coccidiosis or bacterial infections, or for helping to maintain the rate of growth in animals subjected to the coccidial challenge.

One of the most problematic diseases in livestock is necrotic enteritis caused by *Clostridium perfringens*. *Clostridium* infections are usually preceded by coccidiosis. Coccidiosis compromises an animal's immune response so that the animal is less able to respond when subsequently exposed to a bacterial infection. However, other factors such as stress, overstocking or saturation of litter can also contribute. Necrotic enteritis is usually treated by supplementing animal feed with water soluble zinc bacitracin, virginamycin or penicillin.

In the description and claims which follow, reference is made to units of protease activity, units of xylanase activity and units of α-amylase activity. These activities in an enzyme premix or liquid enzyme mix are assayed as follows.

Assay Method for Protease Activity

One unit of protease activity is the amount of enzyme which liberates from the substrate one microgram of phenolic compound (expressed as tyrosine equivalents) in one minute under the conditions described.

Reagents 1. 0.6% (w/v) casein substrate
- Weigh 0.6 g of dry Hammarsten Casein (Merck 2242) into a 200 ml beaker. Moisten with a small amount (about 5 ml) of distilled water. When casein is thoroughly moistened add 20 ml of 0.2 M disodium hydrogen phosphate solution. Warm the mixture at +60° C. with stirring until casein dissolves and an opal solution is obtained. Add 60 ml of distilled water and if needed 1–2 drops of octyl alcohol (anti-foam agent; similar products can be used). After cooling to room temperature, adjust the pH to 7.5 with 0.5 M sodium hydroxide and 1 M lactic acid. Transfer solution into a volumeric flask and fill to 100 ml with distilled water.
- Substrate solution is usable for one week if stored in a cold room.

2. 0.2 M $Na_2HPO_4$ solution
- Dissolve 17.80 g of disodium hydrogen phosphate dihydrate in distilled water and fill to 500 ml with distilled water.

3. 0.02 M NaCl solution
- Dissolve 1.168 g of sodium chloride in distilled water and fill to 1000 ml with distilled water.

4. Precipitation reagent (TCA)
- Dissolve 18.80 g of trichloroacetic acid ($CCl_3COOH$), 18.10 g of anhydrous sodium acetate ($CH_3COONa$) and 18.80 g of acetic acid ($CH_3COOH$) in distilled water and fill to 1000 ml with distilled water.

5. Phenol reagent
- Mix one (1) part of Folin-Ciocalteau phenol reagent with one (1) part of distilled water just prior to the assay.

6. 0.55 M $Na_2CO_3$ solution
- Dissolve 58.295 g of disodium carbonate in distilled water and fill to 1000 ml with distilled water.

Procedure 1. Enzyme sample
- Equilibrate 1 ml of enzyme dilution (in 0.02 M NaCl solution) at +40° C. (for about 5 minutes). Add 5 ml of equilibrated casein substrate, stir and incubate at +40° C. for exactly 30 minutes. Add 5 ml of precipitation reagent and stir. Incubate at +40° C. for exactly 30 minutes and filter immediately with filter paper (Whatman 1 or Macherey Nagel 640 we).
- Pipette 2 ml of filtrate, 5 ml of 0.55 M $Na_2CO_3$ solution and 1 ml of phenol reagent. Stir and incubate at +40° C. for 30 minutes. Cool to room temperature and measure the absorbance at 660 nm against distilled water.

2. Enzyme blank
- Equilibrate 1 ml of enzyme dilution (in 0.02 M NaCl solution) at +40° C. (for about 5 minutes). Add 5 ml of precipitation reagent, stir and incubate at +40° C. for exactly 30 minutes. Add 5 ml of casein substrate, stir and incubate at +40° C. for exactly 30 minutes. Filter immediately with filter paper (Whatman 1 or Macherey Nagel 640 we).
- Treat the filtrate as the enzyme sample.
- The absorbance difference between the enzyme sample and the enzyme blank should be 0.2–0.5.

3. Standard curve
- Prepare a tyrosine stock solution by weighing 10 mg of L-tyrosine into a volumetric flask, dissolve in 0.02 M NaCl solution and fill to 100 ml with 0.02 M NaCl solution.
- Prepare dilutions from tyrosine stock solution in 0.02 M NaCl solution as follows:
  1:50=2 μg/ml
  1:20=5 μg/ml
  1:10=10 μg/ml
  1:5=20 μg/ml
  1:3=33 μg/ml
  1:2=50 μg/ml
- Pipette 2 ml of each tyrosine dilution, 5 ml of 0.55 M $Na_2CO_3$ solution and 1 ml of phenol reagent. Stir and incubate at +40° C. for 30 minutes. Cool to room temperature and measure the absorbance at 660 nm against distilled water.
- Plot tyrosine concentration as a function of absorbance.

Calculation The protease activity of the sample is calculated according to the following equation:

$$\text{Activity}(U/g) = \frac{[A(X) - A(O)] \times k \times F \times Df}{t}$$

wherein:
A(X)=absorbance of the enzyme sample
A(O)=absorbance of the enzyme blank
k=the slope of the standard curve
F=reaction dilution factor (=11)
Df=dilution factor (ml/g)
t=reaction time (30 minutes)

Assay Method for Xylanase Activity

One unit of xylanase activity is the amount of enzyme which liberates one μmol of reducing sugars (expressed as xylose equivalents) from the substrate in one minute under the conditions described.

Reagents 1. 1% (w/v) xylan substrate
- Add 10 ml of 0.5 M sodium hydroxide to 1.0 g of xylan (Fluka 95590). Mix for 30 minutes with a magnetic stirrer. Add about 40 ml of 0.05 M sodium acetate buffer, pH 5.3. Adjust pH to 5.3 with 1 M acetic acid. Fill to 100 ml with 0.05 M sodium acetate buffer, pH 5.3. Substrate should be mixed all the time when used.

2. 1 M acetic acid
- Pipette 5.7 ml of glacial acetic acid into a volumetric flask and fill to 100 ml with distilled water.

3. 0.05 M sodium acetate buffer, pH 5.3
A. Dissolve 4.1 g of sodium acetate in distilled water and fill to 1000 ml with distilled water.

B. Dissolve 3.0 g of glacial acetic acid in distilled water and fill to 1000 ml with distilled water.

Adjust the pH of solution A to pH 5.3 with solution B.

4. Dinitrosalicylic acid (DNS) reagent

Suspend 20.0 g of 3,5-dinitrosalicylic acid in about 800 ml of distilled water. Add gradually 300 ml of sodium hydroxide solution (32.0 g NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until the solution is clear.

Fill to 2000 ml with distilled water and filter through a coarse sintered glass filter.

Store in a dark bottle at room temperature. The Reagent is stable for a maximum of 6 months.

Procedure 1. Enzyme sample 1 ml of enzyme dilution (in 0.05 M sodium acetate buffer, pH 5.3) is equilibrated at +50° C. Add 1 ml of xylan substrate, stir and incubate at +50° C. for exactly 30 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme blank

Incubate 1 ml of xylan substrate at +50° C. for 30 minutes Add 3 ml of DNS-solution and stir. Add 1 ml of enzyme dilution (in 0.05 M sodium acetate buffer, pH 5.3) and stir. Boil the mixture for exactly 5 minutes. Cool the reaction mixture in a cold water bath to room temperature and measure the absorbance at 540 nm against distilled water.

The absorbance difference between the enzyme sample and enzyme blank should be 0.3–0.5.

3. Standard curve

Prepare standard solutions from anhydrous xylose in 0.05 M sodium acetate buffer, pH 5.3. Xylose concentration in the standards should be 0.05–0.5 mg/ml. Pippette 1 ml of standard solution, 1 ml of xylan substrate and 3 ml of DNS-reagent into a test tube. Stir and boil for exactly 5 minutes. Cool in a cold water bath to room temperature and measure the absorbance at 540 nm against standard blank. In the standard blank, xylose solution is replaced by 1 ml of 0.05 M sodium acetate buffer, pH 5.3. Otherwise standard blank is treated like xylose standard.

Plot xylose concentration as a function of absorbance. New standard curve is prepared for every new DNS-reagent.

Calculation The xylanase activity of the sample is calculated according to the following equation:

$$\text{Activity}(U/g) = \frac{([A(X) - A(O)] \times k + C_o) \times 1000 \times Df}{MW_{xyl} \times t}$$

wherein:

A(X)=absorbance of the enzyme sample

A(O)=absorbance of the enzyme blank k=the slope of the standard curve $C_o$=the intercept of xylose standard curve 1000=factor, mmol->$\mu$mol Df=dilution factor (ml/g)

$MW_{xyl}$=molecular weight of xylose (150.13 mg/mmol)

t=reaction time (30 minutes)

Assay Method for α-Amylase Activity

One unit of α-amylase activity catalyses one micromole of hydrolysis of glycosidic linkages in one minute under the conditions described.

Reagents 1. Substrate

As a substrate Phadebas Amylase Test-tablet for in vitro diagnostic use (Pharmacia Diagnostics) is used. The tables are made in distilled water from water insoluble blue starch polymer, bovine serum albumin and buffer.

2. Reagent solution

Dilute 9.0 g of sodium chloride, 2.0 g of bovine serum albumin and 2.2 g of calcium chloride in distilled water in a volumetric flask and fill to 1000 ml with distilled water.

3. 0.5 M NaOH solution

Dissolve 20.0 g of sodium hydroxide in distilled water in a volumetric flask and fill with distilled water to 1000 ml.

4. Filter Paper

Macherey Nagel 640 mn or equal.

Procedure 1. Enzyme sample

Pipette 200 $\mu$l of suitable enzyme dilution in reagent solution and 4.0 ml of reagent solution into test tube. Equilibrate at +37° C. for 5 min. Add the substrate tablet with pincers and mix well for 10 seconds. Incubate at +37° C. for exactly 15 min. The reaction time starts with the addition of the tablet. Add 1.0 ml of 0.5 M NaOH solution and stir well. Filter or centrifuge at 3500 rpm 10 mins and measure the absorbance against reagent blank at 620 nm.

The absorbance of the enzyme sample should be 0.3–0.5.

2. Reagent blank

Equilibrate 4.2 ml of reagent solution at +37° C. for 5 min. Add the substrate tablet with pincers and stir well for 10 seconds. Incubate at +37° C. for exactly 15 min. Add 1.0 ml of 0.5 M NaOH solution, stir well and filter or centrifuge at 3500 rpm for 10 mins.

Calculation The absorbance of sample is proportional to the α-amylase activity. The α-amylase activity of enzyme dilution is read from a table enclosed in the tablet kit. For each tablet batch a calibrated table is supplied.

The α-amylase activity of the sample is calculated as follows:

$$\text{Activity}(U/g) = \frac{\text{Act} \times Df}{1000}$$

where:

Act=α-amylase activity value (expressed U/l) of enzyme dilution read from Phadebas Amylase Test table Df=dilution factor (ml/g)

1000=factor, to convert litres to ml

It is a first object of the present invention to provide a combination of compounds for inclusion in an animal feed which improves the rate of weight gain of healthy animals. It is a second object to provide the use of such a combination for the manufacture of an agent for the prevention and/or treatment of coccidiosis or of bacterial infections such as necrotic enteritis. It is a third object to provide a combination of additives for an animal feed which counters the effect of an *Eimeria* challenge depressing the rate of weight gain of an animal.

Accordingly, a first aspect of the present invention provides the use of a protease and an inner salt of a quaternary amine carboxylic acid for the manufacture of an agent for the treatment and/or prophylaxis of coccidiosis, particularly when caused by *Eimeria* infection.

According to a second aspect, the present invention provides the use of a protease and an inner salt of a quaternary amine carboxylic acid for the manufacture of an agent for the treatment and/or prophylaxis of a bacterial infection, e.g. an infection caused by *Salmonella, Campylobacter or Listeria*.

According to a third aspect, the present invention provides the use of a protease and an inner salt of a quaternary amine carboxylic acid for the manufacture of an agent for the treatment and/or prophylaxis of necrotic enteritis resulting from inter alia *Clostridium perfringens* infection.

According to a fourth aspect, the present invention provides an additive for an animal feed comprising a protease and an inner salt of a quaternary amine carboxylic acid.

In each of the above first-fourth aspects, it is particularly preferred that the agent or additive further comprises a xylanase.

In the following description, reference is made to various methodologies which constitute the common general knowledge of those skilled in the art of veterinary immunology and immunopathology, vaccines, animal pharmacy and animal husbandry. Publications and other materials setting forth such known methodologies include:

General principles of veterinary science are set forth, for example, in The Merck Veterinary Manual, 6th Edition, edited by Fraser et al., 1986; the Food and Drug Administration's FDA 1994 Feed Additive Compendium, U.S. Food and Drug Administration, 1994; Trends in Veterinary Research and Development, part 6, Anti-coccidials, edited by Lloyd-Evans, L. P. M., PJB Publications Ltd., 1991; Diseases of Poultry, edited by B. W. Calnek, Iowa State University Press, Ames, Iowa, 1991.

General principles of animal husbandry are set forth, for example, in H. Patrick et al., Poultry: Feeds & Nutrition, Second Edition, AVI Publishing Co. Inc., Westport, Conn. (1980).

General principles of pharmaceutical sciences are set forth, for example, in Remington's Pharmaceutical Sciences (18th edition, A. R. Gennaro, ed., Mack Publishing, Easton, Pa. 1990).

As mentioned above, the present invention provides for the use of a protease and an inner salt of a quaternary amine carboxylic acid for the manufacture of an agent for the treatment and/or prophylaxis of coccidiosis, bacterial infection or necrotic enteritis resulting from inter alia *Clostridium perfringens* infection. The advantage of using feeds containing a combination of betaine and a protease for rearing animals is that the amount of antimicrobial drugs which have previously been routinely incorporated into feeds can be reduced, or in some cases omitted entirely. In countries where such drugs are banned, it represents a new approach to the control of bacterial diseases.

When omitting antibiotics from an animal's diet there are several potential further benefits. It has previously been necessary to withdraw antibiotics from the animal's diet for a certain time prior to slaughter. This ensures that the meat is relatively free from such drugs and thus fit for human consumption. In contrast, if antibiotics are entirely omitted from an animal's diet, as may be achieved with the present invention, then the animal can be slaughtered at any age rather than after a certain withdrawal period. This affords a farmer improved flexibility and removes the risk of animals becoming infected shortly prior to slaughter. Further, meat and eggs can be guaranteed free of antibiotics. Such meat and eggs have a market advantage as compared to products which cannot be endorsed with such a guarantee.

The present invention also has benefits for human health. Its use reduces the selection pressure for antibiotic-resistant strains of bacteria, by allowing antibiotics to be removed from animal feed. Accordingly, more antibiotic-susceptible strains will be present in the gut of the animal, thereby ensuring a more likely lethal effect in the event of antibiotics being used on the equivalent human condition.

The feed additive according to the present invention can be prepared in a number of ways. For instance, it can be prepared simply by mixing the different appropriate compounds to produce the additive. This can then be either mixed directly with a feed, or more conventionally impregnated onto a cereal-based carrier material such as milled wheat, maize or soya flour. Such an impregnated carrier also constitutes a feed additive in accordance with the fourth aspect of the present invention.

The feed additive may be mixed directly with the animal feed, or alternatively mixed with one or more other feed additives such as a vitamin feed additive, a mineral feed additive or an amino acid feed additive. The resulting feed additive including several different types of components can then be mixed in an appropriate amount with the feed. It is also possible to include the feed additive in the animal's diet by incorporating it into a second (and different) feed or drinking water which the animal also has access to. Accordingly, it is not essential that the additive provided by the present invention is incorporated into the usual cereal-based main feed of an animal, although such incorporation forms a particularly preferred aspect of the present invention.

The feed additive provided by the present invention can be formulated as a pre-mix together with any other enzymes which it is desired to include. The pre-mix can be added to the raw materials before feed manufacture, during feed manufacture or as a final step once the feed is otherwise ready for use. It is possible to add the combination of the inner salt and protease directly to a feed material pre-formed as pellets or as a mash.

If the additive of the present invention is incorporated into an animal feed, then the feed should comprise at least 25% by weight of a cereal, and preferably at least 35% by weight of the cereal. The cereal may be any one or more of wheat, maize, rye, barley, oats, triticale, rice, and sorghum. It is particularly preferred that the cereal is maize or wheat. If the cereal is maize, then the additive or agent preferably further comprises an α-amylase.

Although the cereal component of a cereal-based diet constitutes a source of protein, it is usually necessary to include sources of supplementary protein in the diet, such as those derived from fishmeal, meatmeal or vegetables. These sources of supplementary protein may constitute up to 50% by weight of the animal feed. Sources of vegetable protein include at least one of full fat soybean, rapeseed, canola, soybean meal, rapeseed meal and canola meal.

An inner salt of a quaternary amine carboxylic acid has the general structural formula $R^1R^2R^3N^+$-L-COO$^-$ wherein the substituents $R^1$, $R^2$ and $R^3$ independently represent any organic radicals, preferably alkyl groups, more preferably alkyl groups having 1–6 carbon atoms, and most preferably are all methyl; the linking group -L represents any organic linking group such as alkoxyalkyl or alkylene, preferably $C_1$-$C_6$ alkylene, and most preferably methylene. Examples of the inner salt of a quaternary amine carboxylic acid include betaine ($Me_3N^+CH_2COO^-$), $Me_3N^+$—$CHMeCOO^-$, $Et_3N^-CH_2COO^-$, $Me_2EtN^-CH_2COO^-$, $Me_3N^+CH_2CH_2COO^-$, $Me_3N^+CH_2OCH_2COO^-$, and $Me_3N^-C(CHMe_2)HCOO^-$. The inner salt is preferably betaine which is commercially available from Finnfeeds under the trade name Betafin®.

The inner salt is preferably included in the feed at the rate of 0.01–20 g per kid of feed, more preferably 0.1–10 g/kg, and most preferably 0.5 to 2 g/kg.

The protease used can be any form of protease, however the use of a subtilisin derived from the *Bacillus subtilis* with an activity of not less than 40.000 U/g is preferred. Such subtilisins are described for example in U.S. Pat. No. 4,760,025 A. The protease is included in the feed in such an amount that the feed has a protease activity corresponding to 100 U to 100,000 U per kg of feed, preferable 500 U to 10,000 U per kg of feed. Suitable proteases include but are not limited to the following commercially available proteases: Novo NEUTRASE™ (commercially available from Novo Nordisk); PURAFECT™ (commercially available from Genencor International, Inc); SAVINASE™ (commercially available from Novo Nordisk); MAXACAL™ (commercially available from Gist-Brocades); DURAZYM™ (commercially available from Novo Nordisk); and MAXAPEM™ (commercially available from Gist Brocades).

In a preferred embodiment of the invention, the agent or additive additionally comprises a xylanase. Xylanases can be derived from fungal sources such as *Trichoderma*, *Aspergillus*, *Humicola*, *Neocallimastix* or *Thermomyces*. It is preferred that the xylanase is the low pI xylanase and/or the high pI xylanase obtainable from *Trichoderma longibrachiatum* such as described in Example 22 of WO 92/06209. Alternatively, the xylanase can also be obtained from a bacterium such as *Bacillus*, *Streptomyces*, *Microtetraspora*, *Clostridium* or *Ruminococcus*. It is also possible that the xylanase may be obtained from a host which has been subjected to genetic manipulation such as by the inclusion of an appropriate gene within a host bacterial or fungal strain. The preferred activity of the xylanase should be about 3000 U/g. Xylanase from *Trichoderma longibrachiatum* with a minimum activity of 3000 U/g is commercially available from Finnfeeds International under the trade name AVIZYME®. The xylanase is included in the feed in such an amount that the feed has a xylanase activity corresponding to 100 U to 100,000 U per kg of feed, preferably an activity of 200 U to 1000 U per kg of feed.

In a further preferred embodiment of the invention, α-amylase may also be present in the agent or additive, particularly in the case that the agent or additive is to be included in a maize-containing feed. Although it is within the scope of the invention to use any form of α-amylase, it is preferred to use α-amylase from *Bacillus subtilis* with a minimum activity of 4000 U/g, α-amylase from *Bacillus subtilis* with a minimum activity of 4000 U/g is commercially available from Finnfeeds International under the trade name AVIZYME®. The α-amylase is included in the feed in such an amount that the feed has an α-amylase activity corresponding to 10 U to 100,000 U per kg of feed, preferably an activity of 100 U to 4,000 U per kg of feed.

The inner salt, protease, and optionally xylanase and/or α-amylase can be mixed together prior to use but can also be applied separately to the feed. A combination of protease, xylanase and α-amylase is commercially available under the trade name AVIZYME® 1510 from Finnfeeds International. A further combination of these enzymes is commercially available as a dry premix under the trade name AVIZYME® 1500. It should be noted that it is generally not advisable to store a protease together with other proteins for an extended period of time as it tends to degrade the latter.

The feed additive of the present invention can be used for a wide variety of animals, but use of the invention is particularly preferred in domestic animals and farm livestock. Animals which may in particular benefit from the invention include poultry (such as chickens, turkeys, ducks and geese), ruminants (such as cattle, horses and sheep), swine (pigs), rodents (such as rabbits) and fish. The invention is particularly useful in respect of broiler chickens.

According to the invention, efficacious levels of the additive of the present invention may be administered to alleviate the adverse effects of any coccidiosis-inducing pathogen, and especially any *Eimeria* species including for example, the *Eimeria* species *necatrix, galloparvonis, meleagrimitis, innocua, meleagridis, subrotunda, dispersa, truncata, acervulina, brunetti, maxima, mitis, praecox* and *tenella*. More particularly, the additive promotes weight gain in an animal infected with *Eimeria*.

According to the invention, efficacious levels of the additive of the present invention may be administered to alleviate the adverse effects in poultry due to infection by *Eimeria* species, especially, the *Eimeria* species *E. acervulina, E. brunetti, E. maxima, E. mitis, E. necatrix, E. praecox* and *E. tenella*.

According to the invention, efficacious levels of the additive of the present invention may be administered to alleviate the adverse effects induced in cattle when infected with a member of the *Eimeria* species, especially, the *Eimeria* species *zuernii, bovis (smithii), ellipsoidlis*.

According to the invention, efficacious levels of the additive of the present invention may be administered to alleviate the adverse effects induced in sheep when infected with a member of the *Eimeria* species including the *Eimeria* species *arloingi A (ovina), weybridgensis (arlongis B), crandallis, ahsata, ovinoidalis, gilruthi*.

According to the invention, efficacious levels of the additive of the present invention may be administered to alleviate the adverse effects induced in goats when infected with a member of the *Eimeria* species including, for example, immunization with the *Eimeria* species *arloingi, faurei, caproina, ninakohlyakimovae, christenseni*.

According to the invention, efficacious levels of the additive of the present invention may be administered to alleviate the adverse effects induced in pigs when infected with a member of the *Eimeria* species including, for example, immunization with the *Eimeria* species *debliecki, scabra, penninuta;* and, including adverse effects induced by a member of the *Isospora* species, for example, *Isospora suis*.

According to the invention, efficacious levels of the additive of the present invention may be administered to alleviate the adverse effects in poultry due to infection by bacteria such as *Clostridium, Salmonella, Campylobacter, E. coli, Listeria* and especially *Clostridium perfringens, Salmonella enteritidis* and *Campylobacter jejuni*. As *Clostridium perfringens* is one of the major causes of necrotic enteritis, the nutritional additive can accordingly be used for the preparation of an agent for the treatment and/or prophylaxis of necrotic enteritis.

Additional pharmaceutical methods may be employed to control the duration of action. Controlled delivery may be accomplished by selecting appropriate macromolecules such as polyesters, polyaminoacids, polypyrrolidone, ethylene vinylacetate, methylcellulose, carboxymethyl-cellulose or protamine sulfate and combining these according to well-established procedures in order to control release. The duration of action of the inner salt and protease may also be controlled by incorporating these agents into particles of polymeric materials such as polyesters, polyaminoacids, hydrogels, poly(lactic acid) or ethylene vinylacetate copolymers. Alternatively, the inner salt and protease may be formulated in microcapsules. Various materials and methods for making and using microcapsules are disclosed in Remington's Pharmaceutical Sciences, (16th edition, A. Oslow, ed., Mack, Easton, Pa. 1980).

In addition to the embodiment of the invention wherein the method for administering the inner salt and the protease to animals is in the form of the animal's dietary feed, the present invention further embodies the use of other compositions containing the inner salt and protease which may be co-administered with any desired composition, including any vaccines, nutrients or medicaments.

EXAMPLES

Example 1

The following Example illustrates the effects when a feed additive of the present invention is incorporated in the feed of healthy animals as well as for the manufacture of an agent for the treatment of *Eimeria* infection.

(a) General Procedure 96 female broiler chicks (Ross 208) were divided into four separate group, each of 24 animals. Feeding treatment was started at day 0, and the birds subjected to an *Eimeria maxima* challenge on day 14. Such a challenge was made by inoculating *E. acervulina* and *E. maxima* oocysts to the crop of the chicks in a 2 ml volume of tap water. The dose per bird was 100,000 oocysts of *E. acervulina* and 50,000 oocysts of *E. maxima*. These two *Eimeria* species are spatially segregated in the intestine: *E. acervulina* infects the duodenum and the early jejunum, whereas *E. maxima* prefers the mid-small intestine: from distal jejunum to mid ileum. The birds were kept in cages between days 0–14 and in open pens with a litter of wood shavings between days 14–21.

The feed provided to the birds was corn-soy based with no coccidiostats. The food was cold-pressed into small friable pellets having a diameter of about 5 mm. Starter feeds were used on days 0–14 and finisher feeds on days 14–21. The additives were sprayed on to feed pellets where appropriate by way of an aqueous solution of betaine (at a dose of 1 g per kg of feed) and an aqueous solution of AVIZYME® 1510 which comprises about 300 U/g of xylanase, 4,000 U/g of protease and 400 U/g of α-amylase available from Finnfeeds International at a dose of 1 g/kg of feed.

The feed compositions used were as follows:

Corn-soy Feed

| Ingredients | Starter | Finisher |
|---|---|---|
| Maize | 60.81% | 61.09% |
| Fishmeal 65 fat | 0.50% | 0.50% |
| Soybean meal 48 | 33.38% | 30.18% |
| Soy oil | 1.09% | 4.18% |
| Salt | 0.39% | 0.32% |
| Sodium bicarbonate | 0.01% | 0.00% |
| D L Methionine | 0.18% | 0.10% |
| Limestone | 1.11% | 1.17% |
| Dicalcium phosphate | 1.53% | 1.46% |
| Vitamin + mineral mix | 1.00% | 1.00% |
| TOTAL | 100.00% | 100.00% |

The nutritional composition of these feeds was as follows:

| Nutrients | Starter | Finisher |
|---|---|---|
| Crude protein % | 21.5 | 20 |
| Poult M E kcal/kg | 2975 | 3175 |
| Pig D E Kcal | 3377.25 | 3500.69 |
| Calcium % | 0.9 | 0.9 |
| Phos % | 0.7 | 0.67 |
| Avail Phos % | 0.42 | 0.4 |
| Fat % | 3.92 | 6.85 |
| Fibre % | 2.59 | 2.49 |
| Met % | 0.52 | 0.42 |
| Cys % | 0.36 | 0.34 |
| Met + Cys % | 0.88 | 0.76 |
| Lys % | 1.17 | 1.07 |
| His % | 0.58 | 0.54 |
| Tryp % | 0.25 | 0.23 |
| Thr % | 0.83 | 0.77 |
| Arg % | 1.44 | 1.33 |
| Iso % | 0.92 | 0.85 |
| Leu % | 1.9 | 1.79 |
| Phe % | 1.06 | 0.98 |
| Tyr % | 0.79 | 0.73 |
| Val % | 1.01 | 0.94 |
| Gly % | 0.89 | 0.83 |
| Phe + Tyr % | 1.84 | 1.72 |
| Na % | 0.18 | 0.15 |
| Cl % | 0.29 | 0.24 |
| K % | 0.92 | 0.85 |
| Linoleic acid % | 1.64 | 2.86 |
| Na + K-Cl (meq/kg) | 232.46 | 214.64 |
| D U A (meq/kg) | 439.53 | 436.23 |
| Magnesium % | 0.2 | 0.18 |

(b) Results

The weight of the birds was measured just before the *Eimeria maxima* challenge at 14 days. Table 1 shows that the use of a combination of betaine and the protease results in an increased weight gain compared to when these compounds are added individually to the feed.

TABLE 1

| Group | Diet | Mean Weight (g) |
|---|---|---|
| A | Control (unsupplemented feed) | 422 |
| B | Betaine supplemented feed (Comparative) | 418 |
| C | Protease supplemented feed (Comparative) | 431 |
| D | Betaine and Protease supplemented feed (Invention) | 442 |

Figure 1:
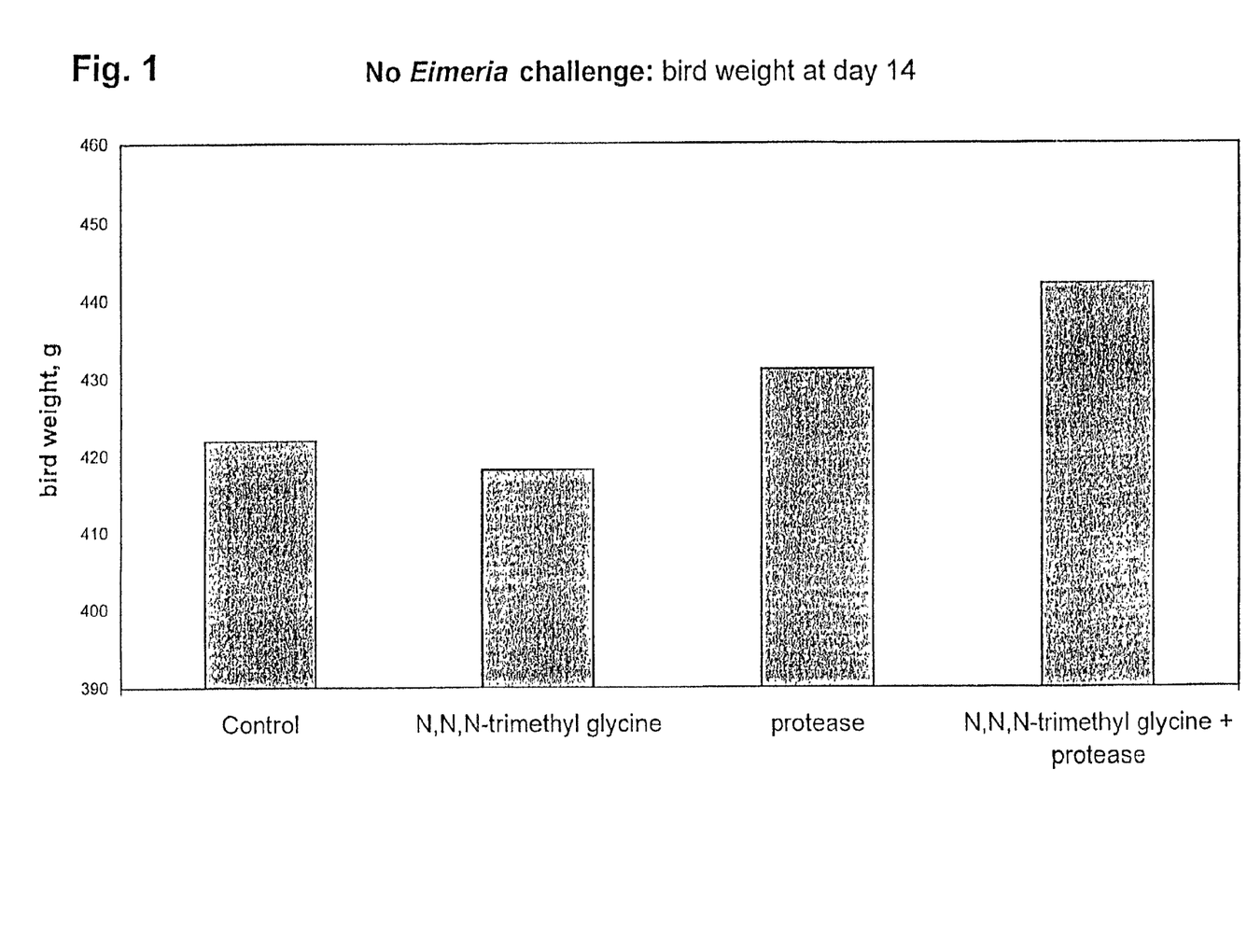
FIG. 1 shows a graphical representation of the effects of supplementing the feed of healthy broiler chickens with betaine; a protease; and with a combination of betaine and a protease.

The results of Table 1 are graphically represented in FIG. 1.

The bird weights were taken again on day 21, i.e. a period of 7 days after the *Eimeria* challenge. The results are summarized in Table 2. An improved weight gain for Group D is observed compared to those of Groups B and C in which the feeds are supplemented by either betaine or protease. Again, a combination of these two components leads to an improvement which is larger than the sum of the effects of the individual components.

TABLE 2

| Group (diet as in Table 1) | Mean Weight (g) |
|---|---|
| A | 651 |
| B | 644 |
| C | 665 |
| D | 690 |

Figure 2:
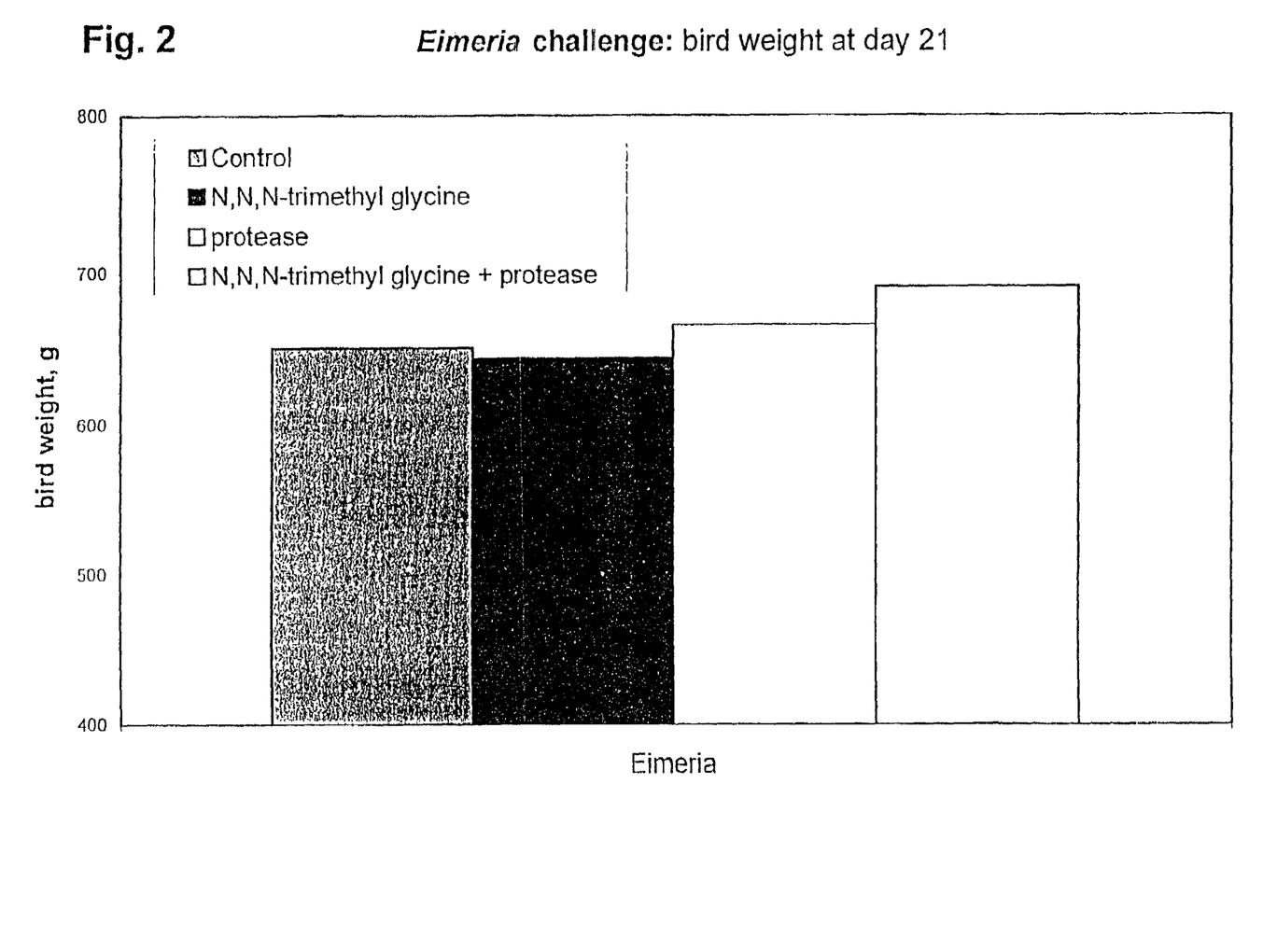
FIG. 2 shows a graphical representation of the effects of supplementing the feed of broiler chicken challenged with *Eimeria maxima* with betaine; a protease; and with a combination of betaine and a protease.

The results set out in Table 2 are graphically represented in FIG. 2.

Example 2

The activity of a combination of betaine and the protease used in Example 1 on *Clostridium perfringens* infection was investigated in this Example. The feed used was the Finisher Feed as described in Example 1.

(a) General Procedure 12 chickens each 21 days old were divided into 3 separate groups, E, F and G, each of 4 birds. Group E were exposed to a challenge of *Eimeria maxima,* Group F to a challenge of *Clostridium perfringens* and Group G to a simultaneous double challenge of *Eimeria* and *Clostridium perfringens.* The *C. perfringens* α-toxin gene was detected from the total microbial DNA as follows: the total microbial DNA of the caecum was subjected to PCR with primers designed according to the known nucleotide sequence of the *C. perfringens* α-toxin gene. The sequence of the α-toxin primers and conditions for performing the PCR reaction are described by Songer and de Meer in Am. J. Vet. Res 1997 July; 58(7), pp 702–705.

(b) Results

Figure 3:
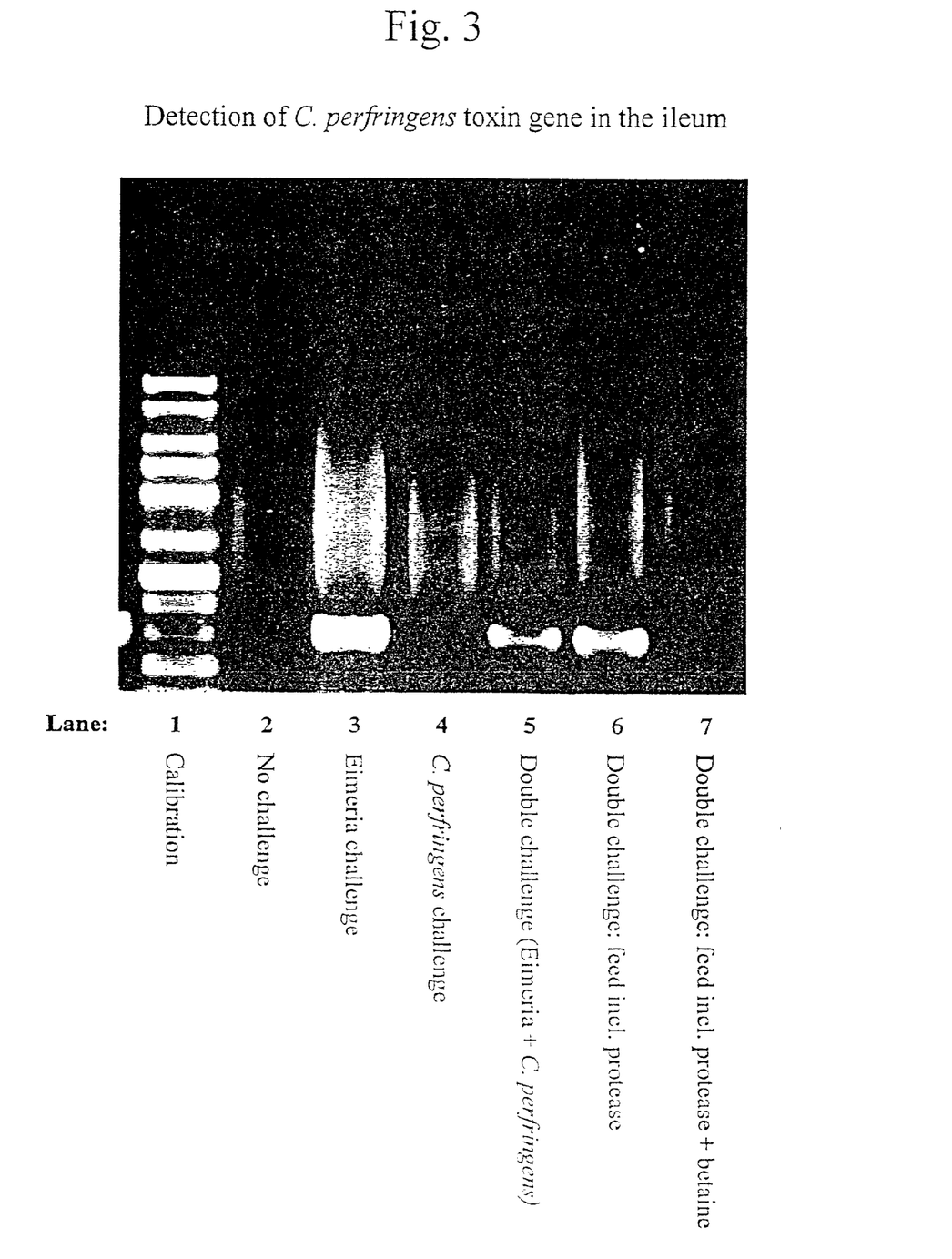
FIG. 3 is a gel chromatogram showing the presence of *C. perfringens* toxin gene in the ileum of chickens fed with variously supplemented feeds and challenged with various pathogens.

The intensive band in lane 3 of the gel shown in FIG. 3 indicates the presence of the α-toxin gene of endogenous *C. perfringens* in the animal. The absence of such bands in lanes 2 and 4 shows that the *Eimeria* challenge is an essential prerequisite for *C. perfringens* infection to take hold. Without wishing to be bound to any theory, it is believed that the *Eimeria* challenge reduces the normal levels of protease in the intestine which then diminishes the nutrient uptake in the upper regions of the intestine and results in increased protein levels (and thus improved growth conditions for *C. perfringens*) in the ileum. A further aspect which might be of significance is the effect of the *Eimeria* challenge on the immune system of the host animal. It is likely that the immune response to a *C. perfringens* challenge is weakened when the immune system is already preoccupied with an *Eimeria* challenge.

A comparison of lanes 6 and 7 in FIG. 3 shows that the band which is indicative of the *C. perfringens* α-toxin gene is only observed for the treatment with protease alone (lane 6) but not for the combined use of betaine and protease (lane 7). It is furthermore general common knowledge in the art that betaine as such is not effective against a *C. perfringens* challenge. Thus, it can be inferred that the combination of betaine and protease is effective against an infection of *C. perfringens* whereas the use of either protease or betaine individually does not result in the *Clostridium* infection being effectively treated.

What is claimed is:

1. A method for treating *Eimeria* infection in an animal, the method comprising feeding the animal a mixture comprising a protease and betaine, wherein the protease and the betaine are in amounts effective for treating or preventing an *Eimeria* infection in the animal.

2. The method of claim 1, wherein the mixture further comprises a xylanase.

3. The method of claim 1, wherein the mixture further comprises an α-amylase.

4. The method of claim 1, wherein the mixture of the betaine and protease further comprises an animal feed to provide an animal feed blend.

5. The method of claim 4, wherein the animal feed blend comprises from 0.01 to 20 grams of betaine per kg of animal feed blend.

6. The method of claim 4, wherein the animal feed blend has a protease activity of 100 to 100,000 U per kg of animal feed blend.

7. The method of claim 4, wherein animal feed blend further comprises a xylanase in an amount effective for providing the animal feed blend with a xylanase activity of 100 to 1000,000 U per kg of animal feed blend.

8. The method of claim 7, wherein the animal feed blend further comprises an α-amylase in amount effective for providing the animal feed blend with a α-amylase activity of 10 to 100,000 U per kg of animal feed blend.

9. The method of claim 7, wherein the animal feed blend further comprises an α-amylase having an α-amylase activity of 10 to 100,000 U per kg of animal feed blend.

10. A method for treating *Eimeria* infection in a chicken, the method comprising feeding the chicken a mixture comprising a protease and betaine, wherein the protease and the inner salt of the carboxylic acid are in amounts effective for treating or preventing an *Eimeria* infection in the chicken.

11. The method of claim 10, wherein the mixture further comprises a xylanase.

12. The method of claim 10, wherein the mixture further comprises an α-amylase.

13. The method of claim 10, wherein the mixture of betaine and protease further comprises an animal feed to provide an animal feed blend.

14. The method of claim 13, wherein the chicken feed blend comprises from 0.01 to 20 grams of betaine per kg of chicken feed blend.

15. The method of claim 13, wherein the chicken feed blend has a protease activity of 100 to 100,000 U per kg of chicken feed blend.

16. The method of claim 13, wherein chicken feed blend further comprises a xylanase in an amount effective for providing the chicken feed blend with a xylanase activity of 100 to 1000,000 U per kg of chicken feed blend.

17. The method of claim 16, wherein the chicken feed blend further comprises an α-amylase in amount effective for providing the chicken feed blend with a α-amylase activity of 10 to 100,000 U per kg of chicken feed blend.

18. The method of claim 16, wherein the chicken feed blend further comprises an α-amylase having an -amylase activity of 10 to 100,000 U per kg of chicken feed blend.

* * * * *

UNITED STATES PATENT AND TRADEMARK OFFICE
CERTIFICATE OF CORRECTION

PATENT NO.         : 7,014,863 B2                                             Page 1 of 1
APPLICATION NO.    : 10/165796
DATED              : March 21, 2006
INVENTOR(S)        : Juha Apajalahti et al.

It is certified that error appears in the above-identified patent and that said Letters Patent is hereby corrected as shown below:

On Title page, Item (56) Assignee: delete "Finfeeds" and insert --Finnfeeds--, therefor.

Signed and Sealed this

Twenty-ninth Day of August, 2006

JON W. DUDAS
*Director of the United States Patent and Trademark Office*